(12) United States Patent
Hansberry et al.

(10) Patent No.: US 9,134,308 B2
(45) Date of Patent: Sep. 15, 2015

(54) ANTIBODY IMMOBILIZATION USING POLY(ETHYLENE GLYCOL) CROSSLINKING

(75) Inventors: David R. Hansberry, Haddonfield, NJ (US); Peter M. Clark, Philadelphia, PA (US); Elisabeth Papazoglou, Yardley, PA (US); Sundar Babu Nadarajan, Ashburn, VA (US); Constantinos Papathomas, legal representative, Yardley, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 13/697,134

(22) PCT Filed: May 12, 2011

(86) PCT No.: PCT/US2011/036290
§ 371 (c)(1),
(2), (4) Date: Mar. 25, 2013

(87) PCT Pub. No.: WO2011/143456
PCT Pub. Date: Nov. 17, 2011

(65) Prior Publication Data
US 2013/0178587 A1    Jul. 11, 2013

Related U.S. Application Data

(60) Provisional application No. 61/334,056, filed on May 12, 2010.

(51) Int. Cl.
| | |
|---|---|
| G01N 33/547 | (2006.01) |
| G01N 33/543 | (2006.01) |
| G01N 33/545 | (2006.01) |
| C07K 17/08 | (2006.01) |

(52) U.S. Cl.
CPC .............. *G01N 33/547* (2013.01); *C07K 17/08* (2013.01); *G01N 33/543* (2013.01); *G01N 33/545* (2013.01); *G01N 33/54313* (2013.01); *G01N 33/54353* (2013.01)

(58) Field of Classification Search
CPC .......... G01N 33/543; G01N 33/54313; G01N 33/54353; G01N 33/545; G01N 33/547
USPC ............ 525/54.1; 435/7.1; 436/528, 531, 532
See application file for complete search history.

(56) References Cited

U.S. PATENT DOCUMENTS

| | | |
|---|---|---|
| 5,217,492 A | 6/1993 | Guire et al. |
| 2006/0068412 A1 | 3/2006 | Tang |
| 2008/0003685 A1 | 1/2008 | Goix et al. |
| 2009/0252703 A1 | 10/2009 | Gegg et al. |
| 2010/0130367 A1 | 5/2010 | Murthy et al. |
| 2013/0034863 A1 | 2/2013 | Papazoglou et al. |

FOREIGN PATENT DOCUMENTS

WO    WO 2010/085658    7/2010

OTHER PUBLICATIONS

Goddard, J.M., et al.; Progress in Polymer Science, 2007, p. 698-725.*
King, D.J.; Applications and Engineering of Monoclonal Antibodies, 1998, p. 58-64.*

* cited by examiner

*Primary Examiner* — Robert Jones, Jr.
(74) *Attorney, Agent, or Firm* — Saul Ewing LLP; Kathryn Doyle; Brian R. Landry (57) ABSTRACT

Provided is a method for immobilizing a macromolecule to a solid support material using poly(ethylene glycol), and a device obtained from the method. The macromolecule can be a polypeptide, such as an antibody.

17 Claims, 7 Drawing Sheets

ANTIBODY IMMOBILIZATION USING POLY(ETHYLENE GLYCOL) CROSSLINKING

CROSS-REFERENCE TO RELATED APPLICATION

This application is the U.S. national phase application filed under 35 U.S.C. §371 claiming benefit to International Patent Application No. PCT/US2011/036290, filed on May 12, 2011, which is entitled to priority under 35 U.S.C. §119(e) to U.S. Provisional Patent Application No. 61/334,056 filed on May 12, 2010, each of which application is hereby incorporated herein by reference in its entirety.

BACKGROUND OF THE INVENTION

A support on which a macromolecule such as a polypeptide has been immobilized is very useful in a variety of diagnostic and research applications. For instance, such supports can be used to purify substances that bind specifically to the immobilized macromolecule or to detect a substance using the macromolecule as a probe. A common application is in immunoassays, such as enzyme-linked immunosorbent assay (ELISA) or sandwich immunoassays. Protein chips and antibody chips are useful for analysis of protein-protein interactions and protein expression profiling. Other uses include chips for high throughput assays, for instance, for identifying potential therapeutics.

There are a number of methods for immobilizing a macromolecule on a support, including passive absorption, polyethyleneimine and EDC/sNHS chemistry. While these methods are useful, there is a need for a method to improve the amount of macromolecule that is immobilized in to a solid support material. This present invention addresses this need.

SUMMARY OF THE INVENTION

The present invention includes a method of immobilizing an antibody to a solid support. The method comprises: i) contacting the solid support with a linear or branched poly(ethylene glycol) (PEG) molecule, wherein the solid support has a surface having a first functional group and, the PEG molecule comprises at least a second and a third functional group and the second functional group reacts with the first functional group to form a covalent bond; ii) contacting the PEG molecule with a crosslinker, wherein the crosslinker comprises glutaraldehyde, and wherein the crosslinker has a fourth and a fifth functional group, wherein the fourth functional group reacts with the third functional group to form a covalent bond; and iii) contacting the crosslinker with the antibody comprising a sixth functional group, wherein the fifth functional group reacts with the sixth functional group to form a covalent bond, thereby immobilizing the antibody to the solid support.

In one embodiment, the PEG molecule is branched, comprising at least two branches and wherein the at least second and third functional groups are at the termini of the at least two branches.

In another embodiment, the solid support material is selected from the group consisting of poly(methyl methacrylate) (PMMA); polystyrene; polycarbonate; polyvinyl chloride (PVC); polyvinyl acetate (PVA); fused silica; glass; a ceramic; a metal; and a semiconductor. In yet another embodiment, the solid support material is PMMA.

In one embodiment the branched PEG molecule comprises at least four branches, wherein each branch comprises a terminal functional group. In yet another embodiment, the PEG molecule has a molecular weight of about 1500 Daltons to about 20,000 Daltons. In yet another embodiment, the first functional group is a carboxyl group. In yet another embodiment, the second and third functional groups are primary amines.

The present invention further includes a device comprising a solid support, a macromolecule and a linear or branched PEG molecule, wherein the macromolecule comprises an antibody, and wherein the PEG molecule is covalently linked to the solid support and the antibody is covalently linked to the PEG molecule.

In one embodiment, the PEG molecule is branched, comprising at least a first and second branch, and wherein the PEG molecule is covalently linked to the solid support by the first branch and the macromolecule is covalently linked to the second branch.

In another embodiment, the solid support material is selected from the group consisting of poly(methyl methacrylate) (PMMA); polystyrene; polycarbonate; polyvinyl chloride (PVC); polyvinyl acetate (PVA); fused silica; glass; a ceramic; a metal; and a semiconductor.

In yet another embodiment, the solid support material is PMMA.

In yet another embodiment, the branched PEG molecule comprises at least four branches, wherein each branch comprises a terminal functional group.

In yet another embodiment, the PEG molecule has a molecular weight of about 1500 Daltons to about 20,000 Daltons.

In yet another embodiment, the macromolecule is covalently linked to the PEG molecule via a crosslinker, and the crosslinker is glutaraldehyde.

In yet another embodiment, the PEG molecule is covalently linked by an amide bond to the solid support.

In yet another embodiment, the macromolecule is covalently linked by an imine bond to the crosslinker.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Described herein is a method for immobilizing a macromolecule comprising a functional group, such as a polypeptide, to a solid support material via a poly(ethylene glycol) molecule. Also described is the resulting device comprising the macromolecule crosslinked to the solid support material. As demonstrated herein, the method provides a significant improvement compared to conventional surface chemistry modifications known in the art. Specifically, the method described herein results in an improvement in the amount of macromolecule, such as an antibody, that is immobilized on the support material. This increase in surface density of immobilized antibody can potentially bind more antigen to the immobilized antibody, for instance, in a sandwich immunoassay, and thus improve the detection sensitivity of the assay. It is contemplated that increasing the surface density for an immobilized macromolecule of interest will be beneficial in any assay or method that involves specifically binding a material to the immobilized macromolecule of interest.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

It is understood that any and all whole or partial integers between any ranges set forth herein are included herein.

As used herein, "macromolecule" refers to polymers and biopolymers including, but not limited to, polypeptides, aptamers, polynucleotides, carbohydrates, lipids and synthetic polymers such as plastics, synthetic fibers and rubber.

A "polynucleotide" means a single strand or parallel and anti-parallel strands of a nucleic acid. Thus, a polynucleotide may be either a single-stranded or a double-stranded nucleic acid. Polynucleotides generally have at least about 50 nucleotides.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer. The term "protein" typically refers to large polypeptides, such as polypeptides having at least about 50 amino acids. The term "peptide" typically refers to short polypeptides, such polypeptides having from about 10 to about 50 amino acids.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

A "solid support material" used herein refers to any solid material that can be activated with functional groups. Solid support materials encompass glass and ceramic materials, metals, semiconductors as well as synthetic polymers such as poly(methyl methacrylate), polystyrene, polycarbonate and the like, as well as natural polymers or biopolymers, for example, carbohydrates, agarose, agar, cellulose, dextran, chitosan, konjac, carrageenan, gellan, alginate, and the like. Solid support materials can be in the form of sheets, chips, particles, beads, strips, tubes, microcapillaries, flow channels, etc. Solid support materials encompass rigid materials, flexible materials, and hydrogel materials.

As used herein, a "functional group" refers to a chemical group within a molecule that is responsible for characteristic chemical reactions. Exemplary functional groups include, but are not limited to, those that contain an oxygen, a nitrogen, a phosphorus or a sulfur atom such primary amines, carboxyls, carbonyls, aldehydes, sulfhydryls, hydroxyl groups and esters.

As used herein, a functional group is reactive with another group if the two groups can react to form a covalent bond.

As used herein, a "branched PEG molecule" refers to the traditional definition of branched polymers (versus linear polymers), wherein a branched PEG molecule is a polymer of two or more linear PEG chains covalently attached to a central core. Each separate PEG chain is referred to herein as a PEG branch or arm. A "branched PEG molecule" encompasses any configuration of PEG chains such as comb-like configurations and brush or bottle-brush configurations.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

A "crosslinker" refers to a linker that joins two other molecules covalently.

By the term "specifically binds," as used herein, is meant a macromolecule which recognizes and binds another molecule, but does not substantially recognize or bind other molecules in a sample. An example is an antibody that specifically binds to an antigen. Another example is a receptor-binding moiety that binds specifically to its cognate receptor.

As used herein, a "receptor-binding moiety" refers to a molecule that binds specifically to a receptor. A receptor-binding moiety may be a naturally-occurring ligand for the receptor or functional derivatives thereof. A receptor-binding moiety may also be a small molecule mimetic of a naturally-occurring ligand, an antibody, a peptidomimetic, an aptamer or any other molecule provided it binds specifically to the receptor and induces receptor-mediated endocytosis of the bound moiety.

As used herein, a "cognate receptor" refers to the receptor to which a given receptor-binding moiety specifically binds. For instance, the folate receptor is the cognate receptor for folate.

Description

The method described herein provides an improvement in the amount of a macromolecule of interest comprising a functional group that can be immobilized to a solid support material such as glass or a polymer material (or to poly(methyl methacrylate) (PMMA). In brief, the method comprises covalently linking poly(ethylene glycol) (PEG) molecules to a surface of the solid support material and crosslinking the macromolecule of interest to the PEG molecules. Thus, the method enables the production of a device having increased amount macromolecule immobilized on a solid support material.

The method comprises contacting an activated surface of a solid support material with a a linear PEG chain comprising two functional groups or a branched poly(ethylene glycol) (PEG) molecule comprising at least two functional groups at the ends of separate PEG branches ("terminal functional group"). An activated solid support material surface refers to a material surface that comprises functional groups such as carboxyl group, a primary amine group, a tosyl group, an epoxy group and the like. At least one functional group on the linear or branched PEG molecule can react with the functional group on the activated surface of the solid support material and form a covalent bond. The at least one other functional group on the linear or branched PEG molecule is reacted with a bifunctional crosslinker, to form a covalent bond. The bifunctional crosslinker comprises at least one functional group that is reactive with the target functional group on the macromolecule of interest. For instance, a polypeptide comprises primary amines. Thus, the crosslinker for a polypeptide macromolecule can comprise at least one amine-reactive functional group that can react with an amine group in a polypeptide, and form a covalent bond. The result is that the macromolecule is covalently linked to the solid support material.

In an embodiment, the method comprises contacting a solid support material that comprises carboxyl groups on the surface to which the macromolecule of interest is to be immobilized with a linear or branched poly(ethylene glycol) (PEG) molecule where each PEG molecule comprises at least two primary amine groups. A carboxyl group on the surface of the solid support material can interact with a primary amine to form an amide bond, thus covalently linking the PEG molecule to the surface of the solid support material. The PEG-modified surface of the support material is subsequently contacted with a bifunctional crosslinker such as glutaraldehyde, wherein both functional groups are amine-reactive. One of the terminal aldehyde groups of the glutaraldehyde molecule reacts with a primary amine on the covalently linked PEG molecule, forming a Schiff base that results in an imine formation. The so-modified surface is then contacted with the macromolecule of interest to be immobilized onto the solid support material surface. The other terminal aldehyde group of the glutaraldehyde molecule can interact with a primary amine in the macromolecule of interest through another Schiff base reaction, thus resulting in the covalent attachment of the macromolecule to the support material. In an alternative embodiment, the bifunctional crosslinker is reacted first with the macromolecule of interest. The resulting product is then reacted with the PEG-modified surface to result in the covalent attachment of the macromolecule of interest to the support material.

Linking reaction chemistries are well known in the art, See, for instance, Thermo Scientific Pierce Crosslinking Technical Handbook (2009, Thermo Fisher Scientific). Thus, the person of skill in the art will recognize that other linking reaction chemistries can be employed in the method described herein. For instance, the support material could be activated to comprise amine groups. The PEG molecule would have at least one amine-reactive functional group on one arm in order to react and link to the activated support material. The other functional group of the PEG molecule can be amine-reactive, or can be a reactive with a different functional group present in the crosslinker. In an embodiment where the macromolecule is a polypeptide having a primary amine functional group, the crosslinker would have one functional group that is amine-reactive in order to react with the molecule of interest and the other functional group a primary amine to react with the PEG molecule. Generally, linking reaction chemistries are selected that operate under conditions that do not adversely affect the components in the method. For instance, if the macromolecule to be immobilized is a polypeptide, linking chemistries that do not require high temperature or extremes in pH are preferred to minimize adverse structural effects on the polypeptide.

Poly(ethylene glycol), commonly known as PEG, refers to an oligomer of ethylene oxide forming a linear chain. PEG molecules useful in the method described herein can be either linear or can be branched, wherein each molecule has at least two and generally three or more PEG branches or arms emanating from a central core group. The PEG molecules in the method comprise at least two functional groups, preferably located at the end of separate arms of the branched molecule. In one embodiment, the PEG molecule is a linear molecule. In another embodiment, the PEG molecule is branched. In some embodiments, the branched PEG molecule comprises 3 to 100 branches, 3 to 50 branches or 3 to 10 branches. In preferred embodiments, substantially all of the arms of a branched PEG molecule terminates in a functional group. The PEG used in the method can have an average molecular weight of about 1500 Dalton to an average molecular weight of about 20,000 Dalton (Da). Exemplified herein are a 1500 Da branched PEG, a 2000 Da branched PEG and a linear 20,000 Da PEG. In an embodiment, the branched PEG molecule comprises 4 arms, each of which terminates in a primary amine.

Bifunctional crosslinkers are well known in the art. Any bifunctional crosslinker known in the art can be used in the method. The crosslinker can comprise two of the same functional groups (homogenous bifunctional crosslinker) or can comprise two different functional groups (heterogeneous bifunctional crosslinker). In an embodiment, the bifunctional crosslinker is a homogenous bifunctional crosslinker and comprises two aldehyde groups. An exemplary crosslinker is glutaraldehyde.

Any solid support material that comprises or can be made to comprise functional groups, thereby being activated, can be used in the practice of the method. Activation of the support material can be achieved by any method in the art, such as coating or contacting with a reagent to form functional groups on the surface. For instance, in an embodiment, the surface of the support material can be activated to comprise carboxyl groups by contacting the surface to with a strong chemical base such as sodium hydroxide. Surface-activated support materials are also commercially available.

The solid support material can be in the shape, for example, of a sheet, a film, a slide, a chip, a disk, a plate, particles, fibers, a tube such as a microcapillary tube. Exemplary materials include, but are not limited to, poly(methyl methacrylate) (PMMA); polyvinyl chloride (PVC); polyvinyl acetate (PVA); polystyrene; fused silica; glass; polymethylpentene; polycarbonate; ceramic materials; metals; and Semiconductors such as silicon wafers and the like. Exemplified herein is PMMA in the form of a flat sheet and in the form of microcapillaries. Thus, in an embodiment, the solid support material in the method and device is PMMA.

Any macromolecule of interest containing at least one functional group, such as a primary amine, a carboxyl, a carbonyl or a sulfhydryl, can be immobilized to a support material using the method described. In preferred embodiments, the macromolecule is a biopolymer and is preferably a polypeptide. In some embodiments, the polypeptide is an antibody. In other embodiments, the polypeptide is a receptor-binding moiety or a cognate receptor.

Figure 1:
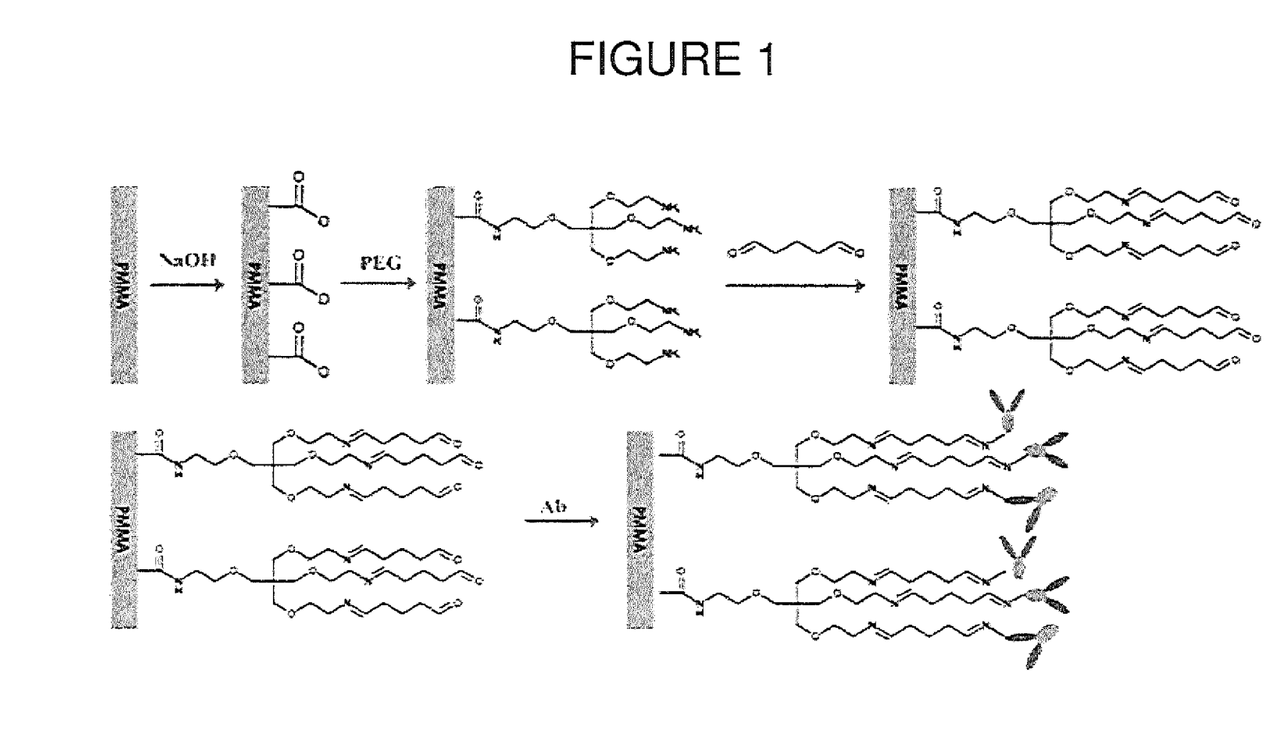
FIG. 1 depicts exemplary reaction chemistries in an embodiment of the method. PMMA=poly(methyl methacrylate). PEG=poly(ethylene glycol). Ab=antibody.

FIG. 1 depicts exemplary reaction chemistries in an embodiment of the method linking an antibody (the macromolecule of interest) to PMMA. The PMMA surface is activated by contacting it with sodium hydroxide (NaOH), leaving carboxyl groups on the PMMA surface. The activated surface is then contacted with a branched PEG having 4 arms, each bearing a terminal primary amine group. A primary amine group of a PEG molecule interacts with a carboxyl group on the PMMA surface to form an amide bond, covalently linking the PEG molecule to the PMMA. The PEG-modified PMMA is then contacted with glutaraldehyde, which reacts with a primary amine on an arm of a PEG. Each PEG arm bearing a terminal primary amine group can react with a glutaraldehyde molecule. The antibody of interest is then introduced and reacts with the second terminal aldehyde of glutaraldehyde, reacting through another Schiff base reaction to covalently link the antibody to the PMMA surface. Each glutaraldehyde molecule linked to a PEG arm can be reacted with an antibody molecule. As depicted in FIG. 1, each functional group on the surface of the PMMA support material can immobilize a total of three antibody molecules due to the intervening branched PEG molecule.

As demonstrated herein, the method described herein improves surface density of immobilization by at least about 10% as compared to conventional methods in the art. The basis for the increase in surface density is not clear. However, it is noted that the improvement is obtained using either a linear PEG molecule or a branched PEG molecule, suggesting that the improvement is not simply or solely due to increasing the number of functional sites available to link to the macromolecule.

The improvement in macromolecular immobilization on a surface is contemplated to improve sensitivity and detection in any qualitative or quantitative assay for detecting a molecule. Exemplary of such assays are immunoassays including, but not limited to, enzyme-linked immunosorbent assay (ELISA), capture ELISA, sandwich assays, and the like, all of which are known to those of skill in the art. See e.g. Harlow et al., 1988, Antibodies: A Laboratory Manual, Cold Spring Harbor Laboratory Press, Cold Spring Harbor, N.Y.; Harlow et al., 1999, Using Antibodies: A Laboratory Manual, Cold Spring Harbor Laboratory Press, Cold Spring Harbor, N.Y.

Moreover, the described method is suitable for use in the quantum dot linked immunosorbent assay (QLISA) described in commonly-assigned International Patent Application No. PCT/US2010/21821, filed Jan. 22, 2010. QLISA is a sensitive assay that can, for instance, detect two or more different biomarkers simultaneously in a nano- or microliter sample. Detection of a biomarker at picogram to nanogram levels is possible with QLISA. As demonstrated herein, QLISA performed with antibody-immobilized devices prepared in accordance with the claimed method advantageously had increased detection sensitivity, as well as high reproducibility, compared to devices prepared according prior art immobilization methods.

The method is further contemplated as suitable for preparing microarrays and chips, including but not limited to protein microarrays and antibody arrays. Protein microarrays are used in multiplex analysis of protein-protein interactions, as well as proteomics. Antibody arrays are useful, for instance, in high throughput profiling of protein expression. The method can also be used to prepare affinity chromatography matrices.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Experiment 1

Immobilization to a Flat Surface of a Solid Support Material

Figure 2:
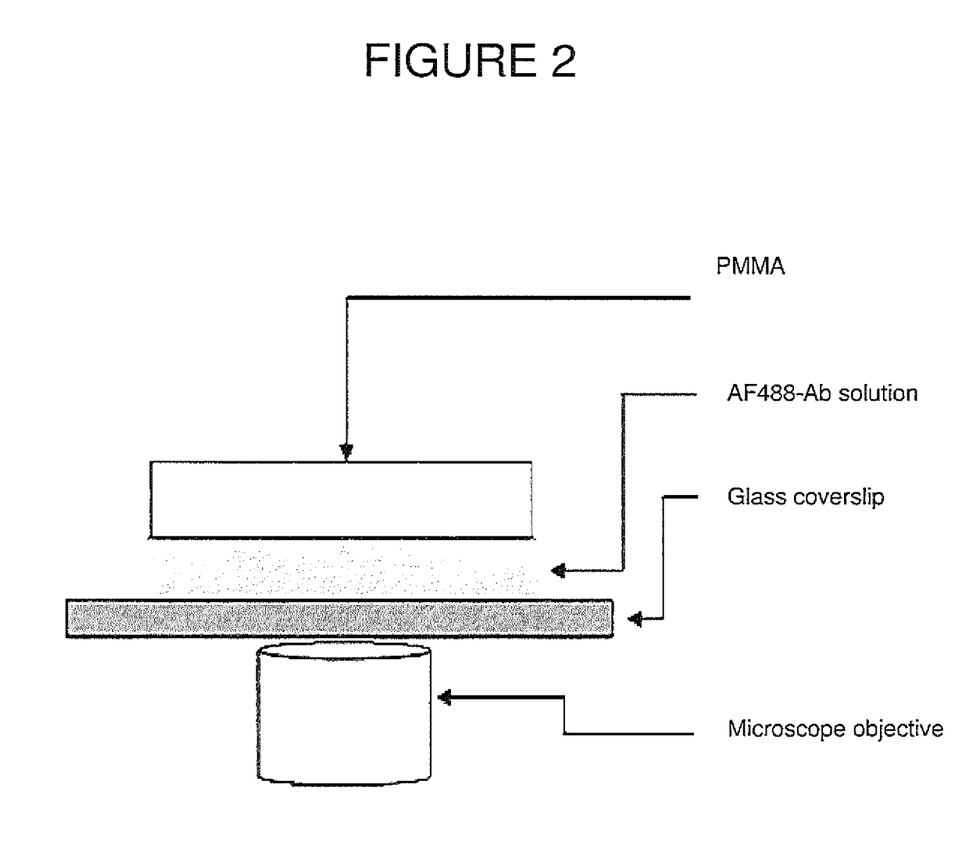
FIG. 2 depicts schematically the imaging configuration used to assess surface density for flat surface experiments.
Figure 3:
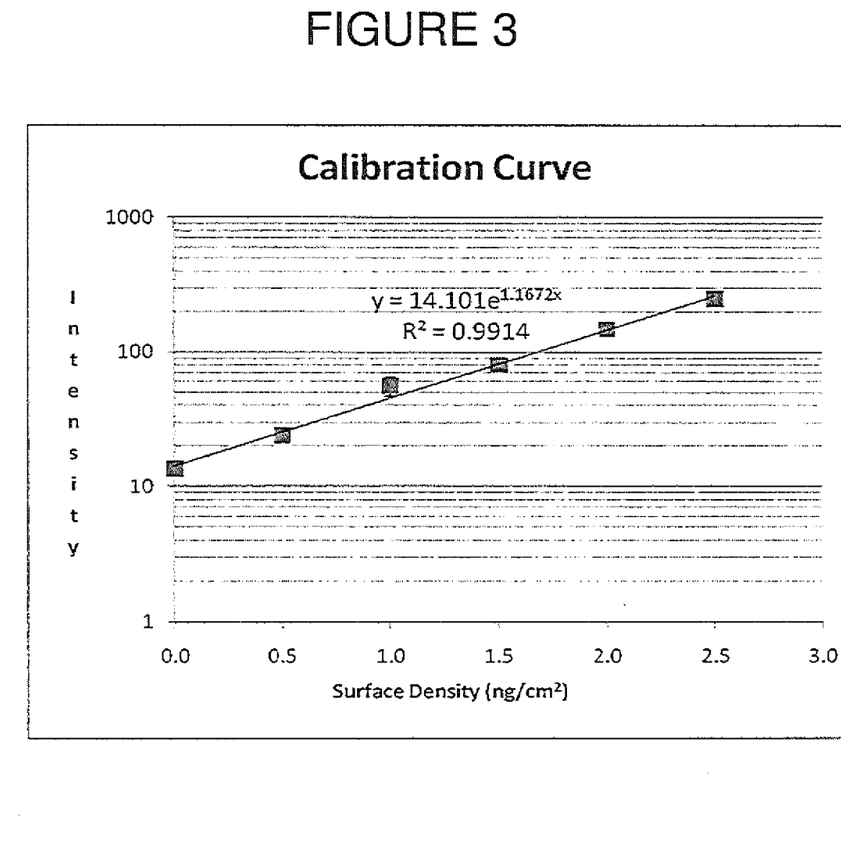
FIG. 3 depicts a calibration curve of fluorescence intensity as a function of surface density.

The materials and methods are first described.
AF488-Ab Conjugation:
Alexa Fluor 488 (AF488) is a fluorescent dye commonly used in bioconjugations with proteins and used as a reporter molecule. AF488 has absorption and emission spectra at 494 nm and 519 nm, respectively. AF488 has a tetrafluorophenyl ester that reacts with the primary amines of Abs. AF488 was conjugated to the primary Ab using Invitrogen's commercially available kit. The AF488-Ab conjugation typically yields 4-9 moles of AF488 per mole of Ab.
Calibration Curve:
Flat poly(methyl methacrylate) (PMMA) squares were cut into 1 cm×1 cm squares and sonicated in isopropyl alcohol for 10 minutes, rinsed with DI water, and air dried prior to use. Alexafluor488-conjugated Ab was diluted to 100, 200, 300, 400 and 500 nanogram per milliliter (ng/mL) and placed on a glass slide with the PMMA square on top. Images were acquired from the fluorescent microscope while maintaining identical microscope parameters. The AF488 is excited and the resulting emission light is filtered with green fluorescent protein and captured for processing. FIG. 2 displays the setup. An exemplary calibration curve is depicted in FIG. 3. The parameters used to generate the calibration curve were used to determine the surface density of immobilized Ab for all subsequent flat surface experiments.

The following examples were prepared to assess immobilization of antibody to a flat surface of poly(methyl methacrylate) (PMMA) using some control conditions as well as using a variety of immobilization methods known in the art. In each of the following examples, PMMA squares were sonicated in isopropyl alcohol for 10 minutes, rinsed with DI water, and air dried prior to use to prepare cleaned PMMA squares. After the antibody incubation, the squares were washed with 0.05% Tween in 1×PBS pH 7.4, and then placed Ab side down on a glass slide, with DI water, and imaged on the fluorescent microscope using the same parameters used to prepare the calibration curve.

Example C1

Passive Adsorption 5 uL of 500 ng/mL of AF488-Ab was placed on each cleaned PMMA square and left for 1 hour.

Example C2

NaOH Only

Cleaned PMMA squares were submerged in 60° C. 1N NaOH for 1 hour while shaking at 100 RPM. The PMMA squares were then rinsed with 1×PBS pH 6.0. 5 uL of 500 ng/mL of AF488-Ab was placed on each treated PMMA square and left for 1 hour.

Example C3

PEI (2 k) Only

Cleaned PMMA squares were submerged in 0.2% PEI (molecular weight of 2,000 Da) for 1 hour while on a shaker at 100 RPM. The squares were then washed with 0.05% 1×PBS pH 7.4. 5 uL of 500 ng/mL of AF488-Ab was placed on each treated PMMA square and left for 1 hour.

Example C4

PEI (25 k) Only

Cleaned PMMA squares are submerged in 0.2% PEI (molecular weight of 25,000 Da) for 1 hour while on a shaker at 100 RPM. The squares were then washed with 0.05% 1×PBS pH 7.4. 5 uL of 500 ng/mL of AF488-Ab was placed on each treated PMMA square and left for 1 hour.

Example C5

1% Glutaraldehyde Only

Cleaned PMMA squares were submerged in 1% glutaraldehyde solution for 30 minutes while on a shaker at 100 RPM. The squares were then washed with 0.05% Tween in 1×PBS pH 7.4. 5 uL of 500 ng/mL of AF488-Ab was placed on each treated PMMA square and left for 1 hour.

Example C6

NaOH, 1% Glutaraldehyde

Cleaned PMMA squares were submerged in 60° C. 1N NaOH for 1 hour while shaking at 100 RPM. The PMMA squares were then rinsed with 1×PBS 6.0. The squares were then submerged in 1% glutaraldehyde solution for 30 minutes while on a shaker at 100 RPM. The squares were then washed with 0.05% Tween in 1×PBS pH 7.4. 5 uL of 500 ng/mL of AF488-Ab was placed on each treated PMMA square and left for 1 hour.

Example C7

PEI (2 k), 1% Glutaraldehyde

PMMA squares are submerged in 0.2% PEI (molecular weight of 2,000 Da) for 1 hour while on a shaker at 100 RPM. The squares were then washed with 0.05% 1×PBS pH 7.4. They were subsequently submerged in 1% glutaraldehyde solution for 30 minutes while on a shaker at 100 RPM. The squares were then washed with 0.05% Tween in 1×PBS pH 7.4. 5 uL of 500 ng/mL of AF488-Ab was placed on each treated PMMA square and left for 1 hour.

Example C8

PEI (25 k), 1% Glutaraldehyde

PMMA squares were submerged in 0.2% PEI (molecular weight of 25,000 Da) for 1 hour while on a shaker at 100 RPM. The squares were then washed with 0.05% 1×PBS pH 7.4. They were then submerged in 1% glutaraldehyde solution for 30 minutes while on a shaker at 100 RPM. The squares were then washed with 0.05% Tween in 1×PBS pH 7.4. 5 uL of 500 ng/mL of AF488-Ab was placed on each treated PMMA square and left for 1 hour.

Example C9

EDC/sNHS

PMMA squares were submerged in 60° C. 1N NaOH for 1 hour while shaking at 100 RPM. The PMMA squares were then rinsed with 1×PBS pH 6.0 and submerged in a solution of 43.4 mM 1-ethyl-3-(3-dimethylaminopropyl)carbodiimide (EDC) and 15.4 mM sulpho-N-hydroxysulfosuccinimide (sNHS) 1×PBS pH 6.0 for 1 hour while on a shaker at 100 RPM. The squares were then washed with 0.05% Tween in 1×PBS pH 7.4. 5 uL of 500 ng/mL of AF488-Ab was placed on each treated PMMA square and left for 1 hour.

Example C10

PEI, 2 k

PMMA squares were submerged in 60° C. 1N NaOH for 1 hour while shaking at 100 RPM. The PMMA squares were then rinsed with 1×PBS 7.4 and submerged in 0.2% polyethyleneimine (PEI; molecular weight of 2,000 Da) for 1 hour while on a shaker at 100 RPM. The squares were then washed with 0.05% 1×PBS pH 7.4. They are then submerged in 1% glutaraldehyde solution for 30 minutes while on a shaker at 100 RPM. The squares were then washed with 0.05% Tween in 1×PBS pH 7.4. 5 uL of 500 ng/mL of AF488-Ab was placed on each treated PMMA square and left for 1 hour.

Example C11

PEI, 25 k

PMMA squares were submerged in 60° C. 1N NaOH for 1 hour while shaking at 100 RPM. The PMMA squares were then rinsed with 1×PBS pH 7.4 and submerged in 0.2% PEI (molecular weight of 25,000 Da) for 1 hour while on a shaker at 100 RPM. The squares were then washed with 0.05% 1×PBS pH 7.4. They are then submerged in 1% glutaraldehyde solution for 30 minutes while on a shaker at 100 RPM. The squares were then washed with 0.05% Tween in 1×PBS pH 7.4. 5 uL of 500 ng/mL of AF488-Ab was placed on each treated PMMA square and left for 1 hour.

The following inventive examples were prepared to assess immobilization of antibody to a flat surface of poly(methyl methacrylate) (PMMA) using the claimed method. In each of the following examples, PMMA squares were sonicated in isopropyl alcohol for 10 minutes, rinsed with DI water, and air dried prior to use to prepare cleaned PMMA squares. After the antibody incubation, the squares were washed with 0.05% Tween in 1×PBS pH 7.4, and then placed Ab side down on a glass slide, with DI water, and imaged on the fluorescent microscope using the same parameters used to prepare the calibration curve.

Example Inv Ex. 1

PEG, 1.5 k

PMMA squares were submerged in 60° C. 1N NaOH for 1 hour while shaking at 100 RPM. The PMMA squares were then rinsed with 1×PBS pH 7.4 and submerged in 0.2% PEG (4-arm amine terminated structure with molecular weight of 1,500 Da from Sigma-Aldrich) for 1 hour while on a shaker at 100 RPM. The squares were then washed with 0.05% 1×PBS pH 7.4. They were then submerged in 1% glutaraldehyde solution for 30 minutes while on a shaker at 100 RPM. The squares were then washed with 0.05% Tween in 1×PBS pH 7.4. 5 uL of 500 ng/mL of AF488-Ab was placed on each treated PMMA square and left for 1 hour Example Inv Ex. 2

PEG, 2 k

PMMA squares were submerged in 60° C. 1N NaOH for 1 hour while shaking at 100 RPM. The PMMA squares were then rinsed with 1×PBS pH 7.4 and submerged in 0.2% di-amino poly(ethylene glycol) (PEG, 4-arm amine terminated structure with molecular weight of 2,000 Da from Sigma-Aldrich) for 1 hour while on a shaker at 100 RPM. The squares were then washed with 0.05% 1×PBS pH 7.4. They were then submerged in 1% glutaraldehyde solution for 30 minutes while on a shaker at 100 RPM. The squares were then washed with 0.05% Tween in 1×PBS pH 7.4. 5 uL of 500 ng/mL of AF488-Ab was placed on each treated PMMA square and left for 1 hour.

Example Inv Ex. 3

PEG, 20 k

PMMA squares were submerged in 60° C. 1N NaOH for 1 hour while shaking at 100 RPM. The PMMA squares were then rinsed with 1×PBS pH 7.4 and submerged in 0.2% PEG (linear chain; molecular weight of 20,000 Da) for 1 hour while on a shaker at 100 RPM. The squares were then washed with 0.05% 1×PBS pH 7.4. They were subsequently submerged in 1% glutaraldehyde solution for 30 minutes while on a shaker at 100 RPM. The squares were then washed with 0.05% Tween in 1×PBS pH 7.4. 5 uL of 500 ng/mL of AF488-Ab was placed on each treated PMMA square and left for 1 hour.

Figure 4:
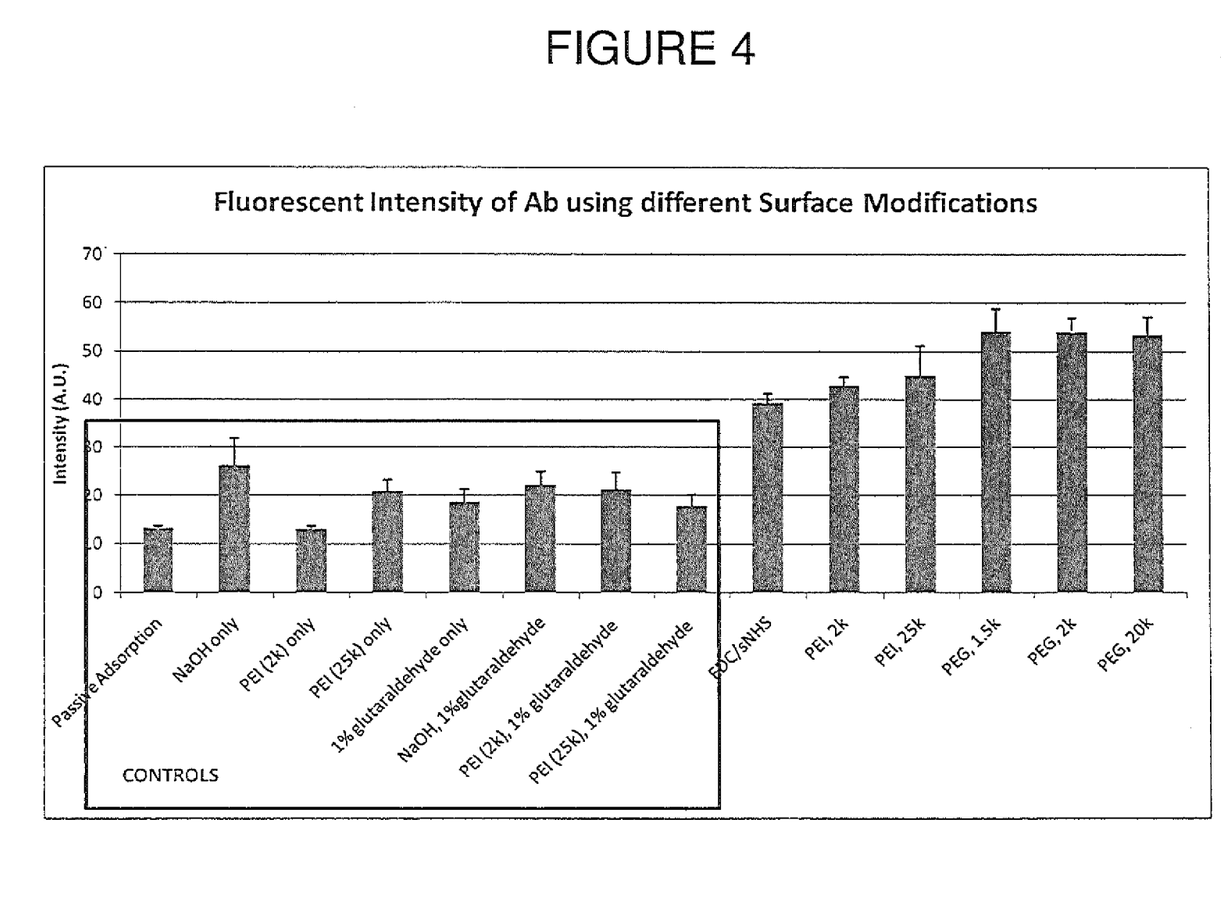
FIG. 4 depicts a bar graph of fluorescence intensity obtained on flat PMMA squares using a variety of immobilization methods for immobilizing Alexafluor488-conjugated antibody to the surface of the PMMA squares. PEI=polyethyleneimine. EDC=1-ethyl-3-(3-dimethylaminopropyl)carbodiimide. sNHS=sulpho-N-hydroxysulfosuccinimide. PEG=poly(ethylene glycol).
Figure 5:
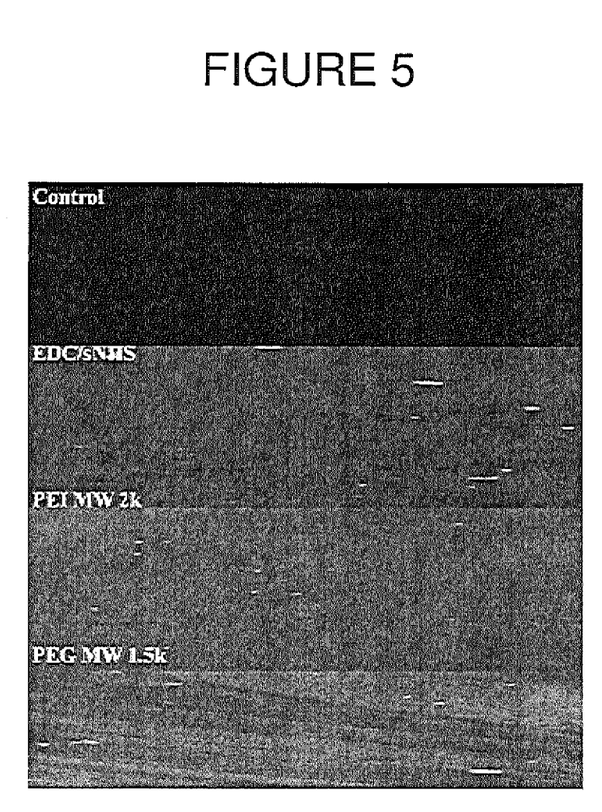
FIG. 5 is an image of four representative fluorescence images for four different methods of immobilizing an antibody to a flat PMMA surface.

The fluorescence intensity data for the above-described examples is shown in FIG. 4. Representative fluorescence images are shown in FIG. 5. Fluorescence intensity measures the amount of antibody bound to the surface area and thus correlates to surface density of the immobilized antibody. Inv. Exs. 1-3 are depicted on the right hand side of the graph. The intensity for these inventive examples is greater than all of the controls (C2-C8) and the prior art methods (C1, and C9-C11) of immobilizing an antibody to a flat surface. These data clearly demonstrate that the method of immobilizing antibody to a flat surface using an intervening branched PEG molecule increases the amount antibody immobilized to the surface of the solid support material.

Figure 6:
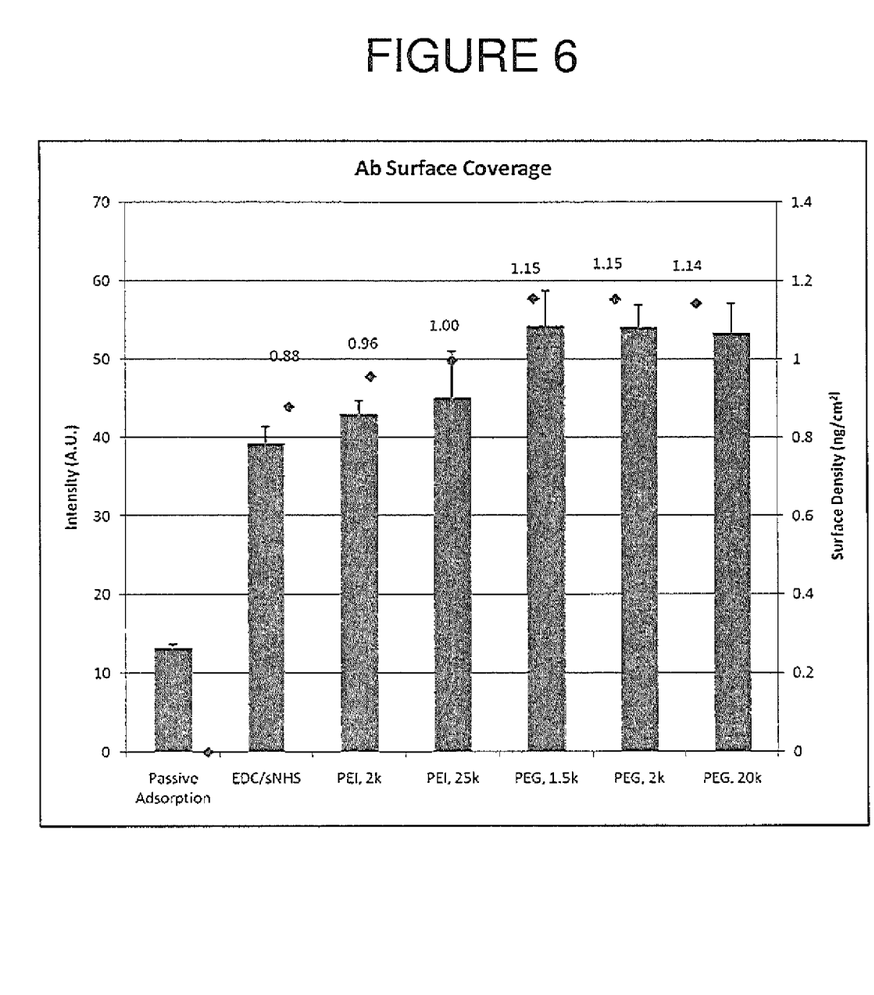
FIG. 6 depicts a bar graph of fluorescence intensity and surface density as a function of immobilization method obtained for immobilizing Alexafluor488-conjugated antibody to the surface of flat PMMA squares. PEI=polyethyleneimine. EDC=1-ethyl-3-(3-dimethylaminopropyl)carbodiimide. sNHS=sulpho-N-hydroxysulfosuccinimide. PEG=poly(ethylene glycol). The number above each bar is the surface intensity.

A subset of the data in FIG. 4 is shown in FIG. 6 showing both intensity and surface density as a function of immobilization method. The PEG/glutaraldehyde method bound over 4 times more antibody than passive adsorption, about 1.3-1.4 times more than 1-ethyl-3-(3-dimethylaminopropyl)carbodiimide (EDC) with sulpho-N-hydroxysulfosuccinimide (sNHS), and about 1.15-1.2 times more than various polyethyleneimines ($p<0.05$). Thus, these date demonstrate an improvement in surface density of at least about 10%, and more, obtained using the claimed method as compared to conventional prior art methods.

Experiment 2

Immobilization to Interior of a Microcapillary Tube

PMMA microcapillaries were rinsed with 60° C. 1N NaOH for 1 hour using a peristaltic pump, followed by a wash with DI water. Next 0.2% di-amino poly(ethylene glycol) (PEG, 4-arm amine terminated structure with molecular weight of 2,000 Da from Sigma-Aldrich) was circulated through the microcapillary for 1 hour at room temperature, followed by a wash with DI water. Next a 1% glutaraldehyde solution was rinsed through the microcapillary for 30 minutes at room temperature, followed by a wash with DI water. Antibody was then circulated through the microcapillary for 1 hour at room temperature, followed by a wash with 0.05% Tween in 1×PBS pH 7.4. This method resulted in antibody covalently bound to the interior surface of the PMMA microcapillaries.

The immobilized antibody microcapillaries were then tested in the QLISA immunoassay. Specifically, an antibody that specifically binds myeloperoxidase (MPO) was immobilized to PMMA microcapillaries. Eleven different human fecal samples were tested. Human fecal samples were collected, aliquoted, and stored at −80° C. until use. Stool samples were thawed, weighed, and then diluted 5 times (v/w) with an extraction buffer (8.359 mg of ethylenediaminetetraacetic acid (EDTA), 250 uL of fetal bovine serum (FBS), 5 mL of glycerol, 12.5 uL of Tween, and 25 mL of 1×PBS pH 7.4). Once the samples were diluted, they were allowed to incubate at 4° C. for 15 minutes. The solution was then homogenized and then incubated again at 4° C. for 15 minutes. This solution was then centrifuged at 4° C. at 14,000 RPM for 30 minutes. The supernatant was collected and diluted 1:10, 1:100, and 1:1000. Samples were then tested with QLISA to determine MPO concentration.

Figure 7:
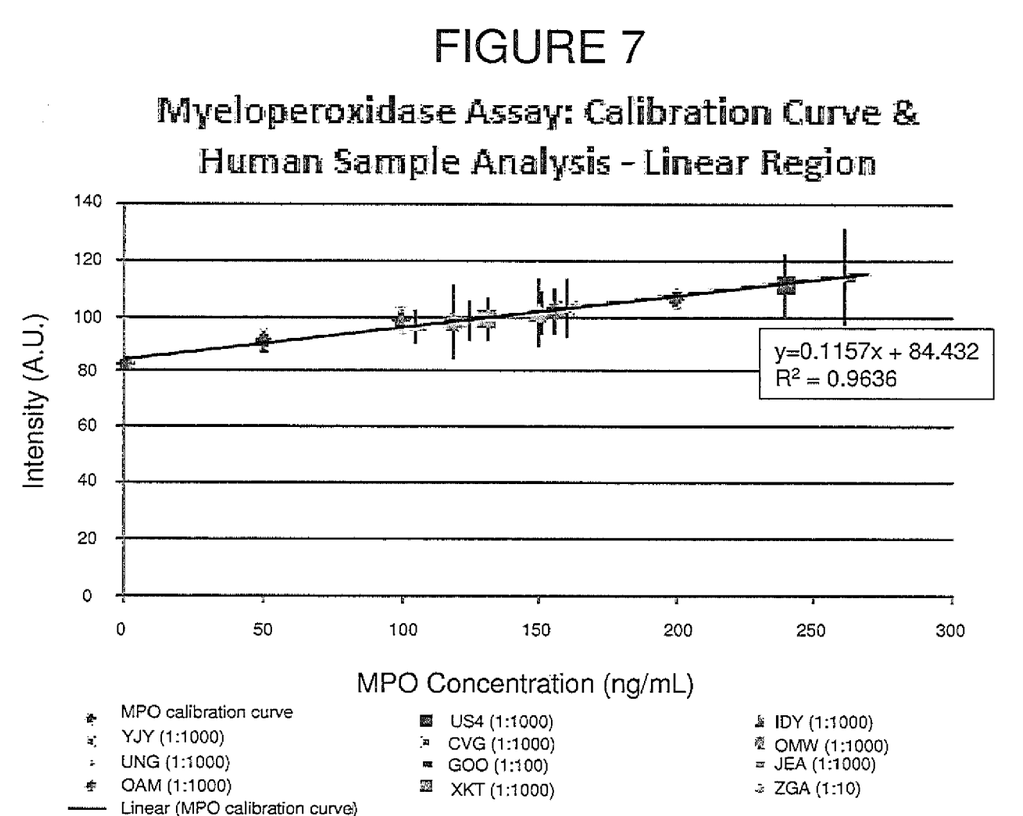
FIG. 7 is a graph fluorescence intensity and myeloperoxidase (MPO) concentration for calibration curve and for several human fecal samples. The line is for the calibration data.

The data are shown in FIG. 7. The MPO detection capabilities in human samples using the devices prepared by the claimed method are comparable to previous clinical findings, which demonstrated that patients with irritable bowel disease have elevated levels of MPO in their stool. Furthermore, using the PEG/glutaraldehyde chemistry to immobilize anti-MPO antibodies to PMMA microcapillaries, there was an MPO lower limit of detection of 35 pM, which represents a threefold increase over the detection limit for the EDC/sNHS chemistry for QLISA. Moreover, the PEG/glutaraldehyde chemistry has shown high reproducibility. At 100 ng/mL, the MPO assay has a precision of 4.1% CV, resulting in 95.5% confidence that 107 ng/mL is statistically different than 100 ng/mL, and 99.8% confidence that 112 ng/mL is different than 100 ng/mL.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of immobilizing an antibody to a solid support at a surface density of 1.14-1.15 ng/cm$^2$, the method comprising:
   i) contacting the solid support with a linear or branched poly(ethylene glycol) (PEG) molecule, wherein the solid support has a surface having a first functional group and, wherein the PEG molecule comprises at least a second and a third functional group and wherein the second functional group reacts with the first functional group to form a covalent bond;
   ii) contacting the PEG molecule with a crosslinker, wherein the crosslinker comprises glutaraldehyde, and wherein the crosslinker has a fourth and a fifth functional group, wherein the fourth functional group reacts with the third functional group to form a covalent bond; and
   iii) contacting the crosslinker with the antibody comprising a sixth functional group, wherein the fifth functional group reacts with the sixth functional group to form a covalent bond, thereby immobilizing the antibody to the solid support, thereby immobilizing the antibody to a solid support at a surface density of 1.14-1.15 ng/cm$^2$.

2. The method of claim 1, wherein the PEG molecule is branched, comprising at least two branches and wherein the at least second and third functional groups are at the termini of the at least two branches.

3. The method of claim 1, wherein the solid support material is selected from the group consisting of poly(methyl methacrylate) (PMMA); polystyrene; polycarbonate; polyvinyl chloride (PVC); polyvinyl acetate (PVA); fused silica; glass; a ceramic; a metal; and a semiconductor.

4. The method of claim 3, wherein the solid support material is PMMA.

5. The method of claim 2, wherein the branched PEG molecule comprises at least four branches, wherein each branch comprises a terminal functional group.

6. The method of claim 1, wherein the PEG molecule has a molecular weight of about 1500 Daltons to about 20,000 Daltons.

7. The method of claim 1, wherein the first functional group is a carboxyl group.

8. The method of claim 7, wherein the second and third functional groups are primary amines.

9. A device comprising a solid support and a macromolecule immobilized to the solid support at a surface density of 1.14-1.15 ng/cm$^2$, the macromolecule comprising an antibody, wherein the antibody is covalently linked to a linear or branched PEG molecule, and wherein the PEG molecule is covalently linked to the solid support.

10. The device of claim 9, wherein the PEG molecule is branched, comprising at least a first and second branch, and wherein the PEG molecule is covalently linked to the solid support by the first branch and the macromolecule is covalently linked to the second branch.

11. The device of claim 9, wherein the solid support material is selected from the group consisting of poly(methyl methacrylate) (PMMA); polystyrene; polycarbonate; polyvinyl chloride (PVC); polyvinyl acetate (PVA); fused silica; glass; a ceramic; a metal; and a semiconductor.

12. The device of claim 11, wherein the solid support material is PMMA.

13. The device of claim 10, wherein the branched PEG molecule comprises at least four branches, wherein each branch comprises a terminal functional group.

14. The device of claim 9, wherein the PEG molecule has a molecular weight of about 1500 Daltons to about 20,000 Daltons.

15. The device of claim 9, wherein the macromolecule is covalently linked to the PEG molecule via a crosslinker, and wherein the crosslinker is glutaraldehyde.

16. The device of claim 9, wherein the PEG molecule is covalently linked by an amide bond to the solid support.

17. The device of claim 11, wherein the macromolecule is covalently linked by an imine bond to the crosslinker.

* * * * *